(12) United States Patent
Carmi et al.

(10) Patent No.: US 10,478,134 B2
(45) Date of Patent: Nov. 19, 2019

(54) SYSTEMS AND METHODS FOR IMPROVED DIAGNOSTICS FOR NUCLEAR MEDICINE IMAGING

(71) Applicant: General Electric Company, Schenectady, NY (US)

(72) Inventors: Raz Carmi, Haifa (IL); Jonathan Sachs, Haifa (IL)

(73) Assignee: GENERAL ELECTRIC COMPANY, Schenectady, NY (US)

(*) Notice: Subject to any disclaimer, the term of this patent is extended or adjusted under 35 U.S.C. 154(b) by 197 days.

(21) Appl. No.: 15/715,666

(22) Filed: Sep. 26, 2017

(65) Prior Publication Data
US 2019/0090826 A1    Mar. 28, 2019

(51) Int. Cl.
| G06F 9/00 | (2006.01) |
| A61B 6/03 | (2006.01) |
| A61B 6/00 | (2006.01) |
| G06T 7/00 | (2017.01) |
| G06T 7/11 | (2017.01) |
| G06F 19/00 | (2018.01) |
| G01T 1/161 | (2006.01) |

(52) U.S. Cl.
CPC ............ *A61B 6/037* (2013.01); *A61B 6/5217* (2013.01); *G01T 1/161* (2013.01); *G06F 19/321* (2013.01); *G06T 7/0012* (2013.01); *G06T 7/11* (2017.01); *G06T 2207/10081* (2013.01); *G06T 2207/10108* (2013.01)

(58) Field of Classification Search
CPC ......... A61B 6/037; A61B 6/06; A61B 6/4266; A61B 6/5217; G01T 1/161; G06F 19/321; G06T 2207/10081; G06T 2207/10108; G06T 7/0012; G06T 7/11
See application file for complete search history.

(56) References Cited

U.S. PATENT DOCUMENTS

2016/0140725 A1    5/2016    Bergner

FOREIGN PATENT DOCUMENTS

| WO | 2015008178 A1 | 1/2015 | |
| WO | WO-2016063235 A2 * | 4/2016 | ............ G06T 19/00 |

OTHER PUBLICATIONS

Yarin Gal; "Uncertainty in Deep Learning", Department of Engineering, University of Cambridge, Sep. 2016, dissertation, (174 pages).

* cited by examiner

*Primary Examiner* — Nirav G Patel
(74) *Attorney, Agent, or Firm* — Dean D. Small; The Small Patent Law Group, LLC

(57) ABSTRACT

Systems and methods described herein generally relate to improved medical diagnostics for nuclear medicine (NM) imaging. The systems and methods define an uncertainty model of a medical imaging system. The uncertainty model is based on natural-statistics distribution of the medical imaging system response. The systems and methods acquire image data of a patient from the medical imaging system, and calculate an uncertainty map of the patient based on the uncertainty model and the image data. The uncertainty map represents a collection of realizations that are generated based on the image data and the uncertainty model. The systems and methods apply a classification or ranking algorithm to the image data and the uncertainty map to calculate image data classification or ranking of the patient including confidence values.

17 Claims, 8 Drawing Sheets

SYSTEMS AND METHODS FOR IMPROVED DIAGNOSTICS FOR NUCLEAR MEDICINE IMAGING

FIELD

Embodiments described herein generally relate to improved medical diagnostics for nuclear medicine (NM) imaging.

BACKGROUND

In nuclear medicine (NM) imaging, such as single photon emission computed tomography (SPECT) or positron emission tomography (PET) imaging, radiopharmaceuticals (RP) are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

However, significant efforts have been invested to develop automated medical diagnostic methods. In NM imaging, the image data are usually subjected to significant noise or uncertainty. A key problem is the uncertainty in a specific patient scan cannot be estimated just from the image results of a single scan. In NM image noise (or reconstruction artifacts such as blobs) can appear similarly to real findings, and even sophisticated filters cannot resolve the noise. For example, measuring standard deviation within a homogenous region on the images, or even on the acquired projections, is not a good indication for the true uncertainty in the data which is usually significantly higher.

BRIEF DESCRIPTION

In an embodiment a method is provided. The method includes defining an uncertainty model of a medical imaging system. The uncertainty model is based on natural-statistics distribution of the medical imaging system response. The method includes acquiring image data of a patient from the medical imaging system, and calculating an uncertainty map of the patient based on the uncertainty model and the image data. The uncertainty map represents a collection of realizations that are generated based on the image data and the uncertainty model. The method includes applying a classification or ranking algorithm to the image data and the uncertainty map to calculate image data classification or ranking of the patient including confidence values.

In an embodiment a medical imaging system is provided. The system includes plurality of detector units disposed about a gantry configured to acquire image data of a patient, and a memory that includes a classification or ranking algorithm. The system includes at least one processor operably coupled to the detector units. The at least one processor is configured to define an uncertainty model of a medical imaging system. The uncertainty model is based on natural-statistics distribution of the medical imaging system response. The at least one processors is configured to acquire image data of a patient from the medical imaging system, and calculate an uncertainty map of the patient based on the uncertainty model and the image data. The uncertainty map represents a collection of realizations that are generated based on the image data and the uncertainty model. The at least one processor is configured to apply a classification or ranking algorithm to the image data and the uncertainty map to calculate image data classification or ranking of the patient including confidence values.

In an embodiment a tangible and non-transitory computer readable medium is provided. The tangible and non-transitory computer readable medium includes one or more programmed instructions configured to direct one or more processors. The one or more processors are directed to define an uncertainty model of a medical imaging system. The uncertainty model is based on natural-statistics distribution of the medical imaging system response. The one or more processors are directed to acquire image data of a patient from the medical imaging system, and calculate an uncertainty map of the patient based on the uncertainty model and the image data. The uncertainty map represents a collection of realizations that are generated based on the image data and the uncertainty model. The one or more processors are directed to applying a classification or ranking algorithm to the image data and the uncertainty map to calculate image data classification or ranking of the patient including confidence values.

DETAILED DESCRIPTION

Figure 1:
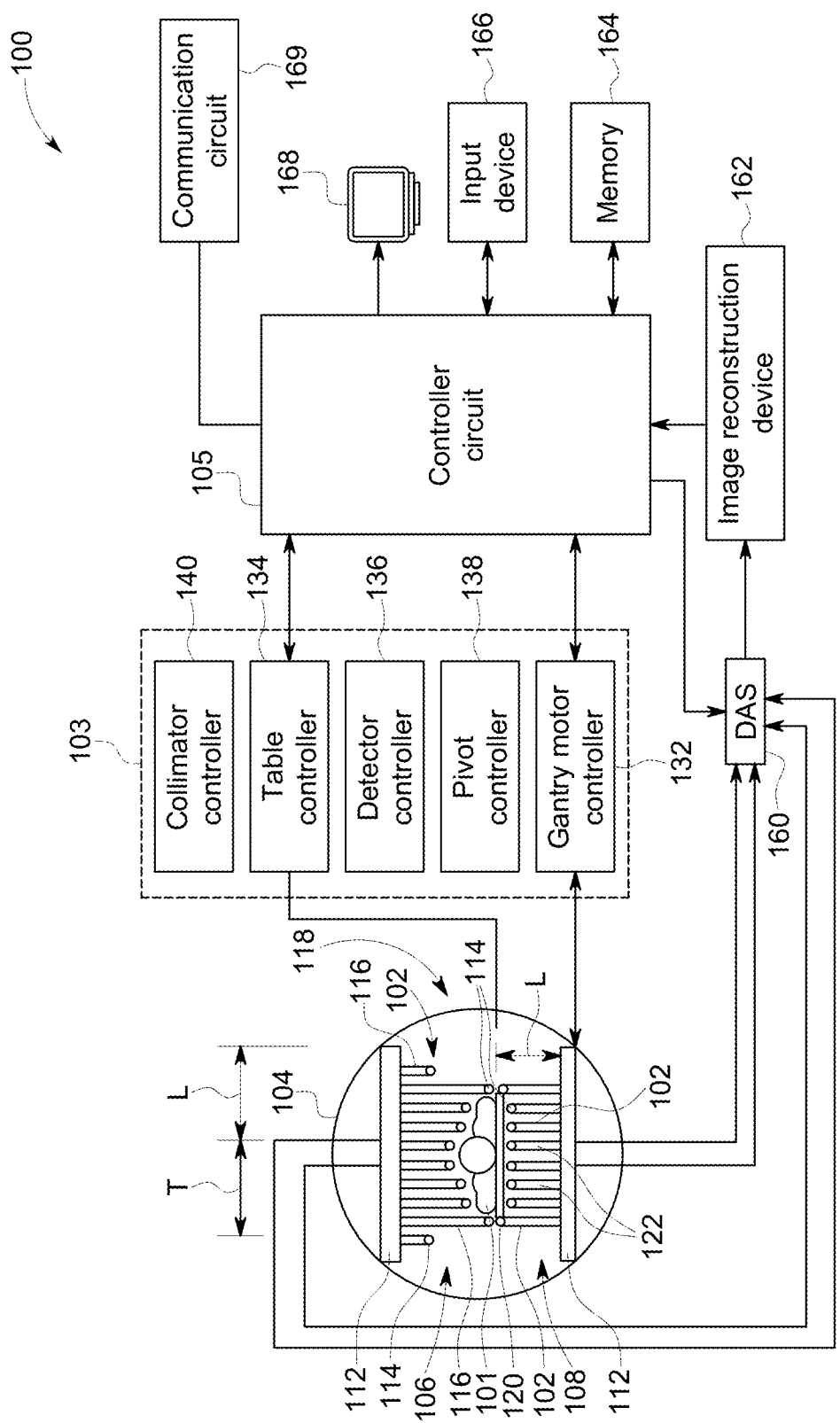
FIG. 1 shows a schematic view of an embodiment of a medical imaging system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for improved medical diagnosis or other analysis results which are based on classification or ranking algorithms. The systems and methods achieve the improvements by providing a systematic and spatially-related calculation of the uncertainty for the nuclear medicine (NM) images. The NM images provide for example, a volumetric map for the specific patient data. The systems and methods generate an uncertainty map based on image data of a patient. The uncertainty map may represent different simulations based on an uncertainty model a subject model derived from the image data of a patient. The simulator is configured to simulate repeated patient scans using the imaging system model and the subject model. The simulator produces different realizations in different regions of an image volume from the image data. The systems and methods apply the image data and the uncertainty map for a classification or ranking algorithm. The classification or ranking algorithm provides a classification or ranking of the patient including confidence values. The classification or ranking represents a severity rank for voxel locations of the image data and/or the uncertainty map. The severity rank is indicative of a predicted diagnosis (e.g., lesion, cancer, benign, fracture) at the voxel location. The confidence values are utilized to affirm and/or reduce a likelihood of the predicted diagnosis. The systems and methods can adjust the severity rank based on the confidence values. The confidence values and the classification or ranking increases diagnostics for the systems and methods described herein.

The embodiments described herein may be implemented in medical imaging systems, such as, for example, SPECT, SPECT-Computed Tomography (CT), SPECT-Magnetic Resonance (MR), PET, PET-CT and PET-MR. Various methods and/or systems (and/or aspects thereof) described herein may be implemented using alternative medical imaging system, such as an ultrasound imaging system, CT, MR imaging, and/or the like.

A technical effect of at least one embodiment includes improved automated predicted diagnosis of a patient. A technical effect of at least one embodiment includes reducing the inherent uncertainty of scans of the patient.

TERMS

The term "uncertainty model" refers to an inherent uncertainty of a medical imaging system, such as a NM imaging system. The uncertainty model represents a statistical distribution of the medical imaging system response to random physical variables. The inherent uncertainty of the medical imaging system may be affected by various factors and is based on the probability that a photon is detected by the electronics of the medical imaging system. The probability is based on a natural-statistics distribution of the medical imaging system. The natural-statistics distribution may represent one or more of a Poisson distribution, a Gaussian distribution, a Lorentzian (Cauchy) distribution, a binomial distribution, and/or the like.

The term "realization" refers to a simulated image that is generated based on image data that is collected and has energy levels within a corresponding range or subset of the energy levels. A realization represents a possible simulation based on the acquired image data that represents a projection and sinogram count value from an uncertainty model.

The term "uncertainty map" refers to a collection of realizations based on a scan of a patient. The collection of realizations represent different simulated outputs based on selections of image data. The selections of image data correspond to different projection and/or sinogram counts from the uncertainty model of the image data. The uncertainty of the uncertainty map refers to different relative standard deviations representing spatial locations within an image volume.

The term "classification and/or ranking algorithm" refers to an artificial intelligence algorithm and/or trained algorithm that is configured to classify and/or rank a severity rank of unhealthy tissue (e.g., lesions, cancer, benign). The severity rank of the unhealthy tissue is indicative of a confidence value that the unhealthy tissue is identified. The classification and/or ranking algorithm learns from various automatic or manual inputs, such as observations and/or data. The classification and/or ranking algorithm can be adjusted over multiple iterations based on the observations and/or data. The classification or ranking algorithm may be based on machine learning models that are trained on multiple pre-classified or ranked example data, including techniques such as: convolutional neural networks, Bayesian neural networks, support vector machine, decision trees, random forest, regression and/or the like. Alternatively, the classification or ranking algorithm may be based on deterministic parameter setting, adjusted by a human expert.

The term "pathology" refers to a portion of an anatomical structure having an irregular and/or structural deviation relative to a healthy anatomical structure. The pathology represents the portion of the anatomical structure having a disease or illness.

The term "anatomical structure" refers to an anatomical part of a patient. Non-limiting examples of an anatomical structure include an organ (e.g., heart, kidney, lung, liver, bladder, brain, neonatal brain, embryo, abdomen, and/or the like), vascular structure (e.g., vein, artery, mitral valve, aortic valve, tricuspid valve, pulmonary valve), tissue or portion of an organ (e.g., breast tissue, liver tissue, brain tissue, cardiac tissue, prostate tissue, and/or the like), skeletal structure, and/or the like.

FIG. 1 is a schematic illustration of a medical imaging system 100, such as a NM imaging system. The medical imaging system 100 includes a plurality of imaging detector head assemblies mounted on a gantry 104 (which may be mounted, for example, in rows, in an iris shape, or other configurations, such as a configuration in which the movable detector carriers 116 are aligned radially toward the patient-body 101). It should be noted that the arrangement of FIG. 1 is provided by way of example for illustrative purposes, and that other arrangements (e.g., detector arrangements) may be employed in various embodiments. In the illustrated example, a plurality of imaging detectors 102 are mounted to the gantry 104. In the illustrated embodiment, the imaging detectors 102 are configured as two separate detector arrays 106 and 108 coupled to the gantry 104 above and below a subject 101 (e.g., a patient), as viewed in FIG. 1. The detector arrays 106 and 108 may be coupled directly to the gantry 104, or may be coupled via support members 112 to the gantry 104 to allow movement of the entire arrays 106 and/or 108 relative to the gantry 104 (e.g., transverse translating movement in the left or right direction as viewed by arrow T in FIG. 1). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 101, such as linearly. Thus, in the illustrated embodiment the detector arrays 106 and 108 are mounted in parallel above and below the subject 101 and allow linear movement of the detector units 114 in one direction (indicated by the arrow L), illustrated as perpendicular to the support member 112 (that are coupled generally horizontally on the gantry 104). However, other configurations and orientations are possible as described herein. It should be noted that the movable detector carrier 116 may be any type of support that allows movement of the detector units 114 relative to the support member 112 and/or gantry 104, which in various embodiments allows the detector units 114 to move linearly towards and away from the support member 112.

Each of the imaging detectors 102 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 102 may include one or more detector units 114 coupled to a respective detector carrier 116 and having dimensions of, for example, 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels (pixelated anodes). In some embodiments, each detector unit 114 includes a plurality of modules, such as an array of 1×7 modules. However, different configurations and array sizes are contemplated including, for example, detector units 114 having multiple rows of modules.

It should be understood that the imaging detectors 102 may be different sizes and/or shapes with respect to each other, such as square, rectangular, circular or other shape. An actual field of view (FOV) of each of the imaging detectors 102 may be directly proportional to the size and shape of the respective imaging detector.

The gantry 104 may be formed with an aperture 118 (e.g., opening or bore) therethrough as illustrated. A patient table 120, such as a patient bed, is configured with a support mechanism (not shown) to support and carry the subject 101 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H" and "L", for example, and may be rotatable about the subject 101. For example, the gantry 104 may be formed as a closed ring or circle, or as an open arc or arch which allows the subject 101 to be easily accessed while imaging and facilitates loading and unloading of the subject 101, as well as reducing claustrophobia in some subjects 101. Additional imaging detectors (not shown) may be positioned to form rows of detector arrays or an arc or ring around the subject 101. By positioning multiple imaging detectors 102 at multiple positions with respect to the subject 101, such as along an imaging axis (e.g., head to toe direction of the subject 101) image data specific for a larger FOV may be acquired more quickly. Each of the imaging detectors 102 has a radiation detection face, which is directed towards the subject 101 or a region of interest within the subject.

The collimators 122 (and detectors) in FIG. 1 are depicted for ease of illustration as single collimators in each detector head. It may be noted that different types of collimators may be used in different columns. Optionally, for embodiments employing one or more parallel-hole collimators, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 103 may control the movement and positioning of the patient table 120, imaging detectors 102 (which may be configured as one or more arms), gantry 104 and/or the collimators 122 (that move with the imaging detectors 102 in various embodiments, being coupled thereto). A range of motion before or during an acquisition, or between different image acquisitions, is set to maintain the actual FOV of each of the imaging detectors 102 directed, for example, towards or "aimed at" a particular area or region of the subject 101 or along the entire subject 101. The motion may be a combined or complex motion in multiple directions simultaneously, concurrently, or sequentially.

The controller unit 103 may have a gantry motor controller 132, table controller 134, detector controller 136, pivot controller 138, and collimator controller 140. The gantry motor controller 132 may move the imaging detectors 102 with respect to the subject 101, for example, individually, in segments or subsets, or simultaneously in a fixed relationship to one another. For example, in some embodiments, the gantry controller 132 may cause the imaging detectors 102 and/or support members 112 to move relative to or rotate about the subject 101, which may include motion of less than or up to 180 degrees (or more).

The controllers 103, 132, 134, 136, 138, 140 may be automatically commanded by a controller circuit 105, manually controlled by an operator, or a combination thereof. Additionally, the controller circuit 105 receives user inputs (e.g., control commands) from a user input device 166, which is provided to receive user inputs (e.g., control commands), as well as a display 168 to display images. The controller circuit 105 is configured to control the operation of the medical imaging system 100. The controller circuit 105 may include one or more processors. Optionally, the controller circuit 105 may include a central processing unit (CPU), one or more microprocessors, a graphics processing unit (GPU), or any other electronic component capable of processing inputted data according to specific logical instructions. Optionally, the controller circuit 105 may include and/or represent one or more hardware circuits or circuitry that include, are connected with, or that both include and are connected with one or more processors, controllers, and/or other hardware logic-based devices. Additionally or alternatively, the controller circuit 105 may execute instructions stored on a tangible and non-transitory computer readable medium (e.g., a memory 164).

The controller circuit 105 is configured to automatically identify a diagnosis of the subject 101, as shown in FIG. 2.

FIGS. 2A-D illustrates a flow chart of an embodiment of a method 200. The method 200, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein.

Beginning at 202, the controller circuit 105 receives medical imaging modality model that includes configuration and image agent properties of the medical imaging system 100. The medical imaging model may represent the type of imaging performed by the medical imaging system 100, such as SPECT, PET, PET-CT, SPECT-CT, and/or the like. The configuration of the medical imaging system 100 represents the parameters such as a geometry of the gantry 104, position of a patient table 120 relative to the gantry 104, type of the plurality of imaging detectors 102, and/or the like. The image agent properties correspond to the radiopharmaceutical (RP) does provided to the patient for imaging. For example, the image agent properties include the gamma ray energy emitted by the RP, a half-life of the RP, and/or the like.

The configuration includes scan parameters that define a system matrix. The system matrix describes a relationship between activity within the imaging volume of the patient and expected observations at the plurality of imaging detectors 102 for a predetermined geometry (e.g., patient size, physiology) and predetermined scan time of the patient. For example, the expected observations represents a probability that a photon will be detected and electronically processed by the imaging detectors 102. The probability represents a likelihood that a specific emitted photon, having a given energy, travel time, and travel direction, will be detected at a detector pixel and translated by the detector electronics. The probabilities can be based on Poisson noise of the medical imaging system 100. The Poisson noise represents random fluctuations in the electronic circuitry of the detectors and/or overall medical imaging system 100.

At 204, the controller circuit 105 defines an uncertainty model of the medical imaging system 100 response. The uncertainty model represents the inherent data collection uncertainty of the medical imaging system 100 response during a period of time (e.g., scan length). For example, the uncertainty model can be based on a natural-statistics distribution from the system matrix. The natural-statistics distribution is based on the conditions (e.g., system matrix, geometry, RP) of the medical imaging system 100. The natural-statistics distribution can represent a Poisson distribution, a Gaussian distribution, a Lorentzian distribution, a binomial distribution, and/or the like. For example, the Poisson distribution can represent a Gaussian curve of different possible counts (e.g., projection counts, sinogram counts, events) versus a probability of getting said count. The probability is associated with the system matrix, which defines a probability that a photon will be detected. The Poisson distribution peaks at a mean value representing a "true value" that is selected for imaging based on the configuration of the medical imaging system 100. The mean value is defined by a number of counts recorded in successive measurements during the scan. Based on the Poisson distribution, the uncertainty model provides a probability of observing N counts during the scan of the patient. In another example, the Lorentzian distribution represents a continuous probability distribution based on the system matrix. The Lorentzian distribution represents a probability distribution that photon will be detected.

At 206, the controller circuit 105 acquires image data and constructs an image volume of the patient (e.g., the subject 101). For example, the image data is acquired during a scan of the patient, after the patient is positioned in the bore 106 of the gantry 104. A length of the scan may be for a default length of time stored in the memory 164. As non-limiting examples, the image data may be indicative of events detected by a PET or SPECT imaging system while in a count or list mode. The patient is administered the RP that causes emission of radiation from the patient. The image data is collected based on a predefined acquisition plan that specifies, among other things, the positions and/or orientations of the plurality of imaging detectors 102. For example, rotational positions based on rotations of the gantry 104 may be specified, as well as positions throughout a sweep or pivot range of the plurality of imaging detectors 102. The acquired image data has values that are distributed over a range of energy levels for the associated photon events. The controller circuit 105 acquires projection counts and/or sinogram counts for each location over the scan of the patient. The controller circuit 105 generates an image volume based on the counts (e.g., image data) acquired during the scan. The image volume represents projection data from the plurality of detector and/or gantry angles acquired from the counts to form a three-dimensional (3D) image.

At 208, the controller circuit 105 determines a subject model of the patient based on the image data. In connection with FIG. 2B, the subject model is formed based on a method 208a.

Figure 2A:
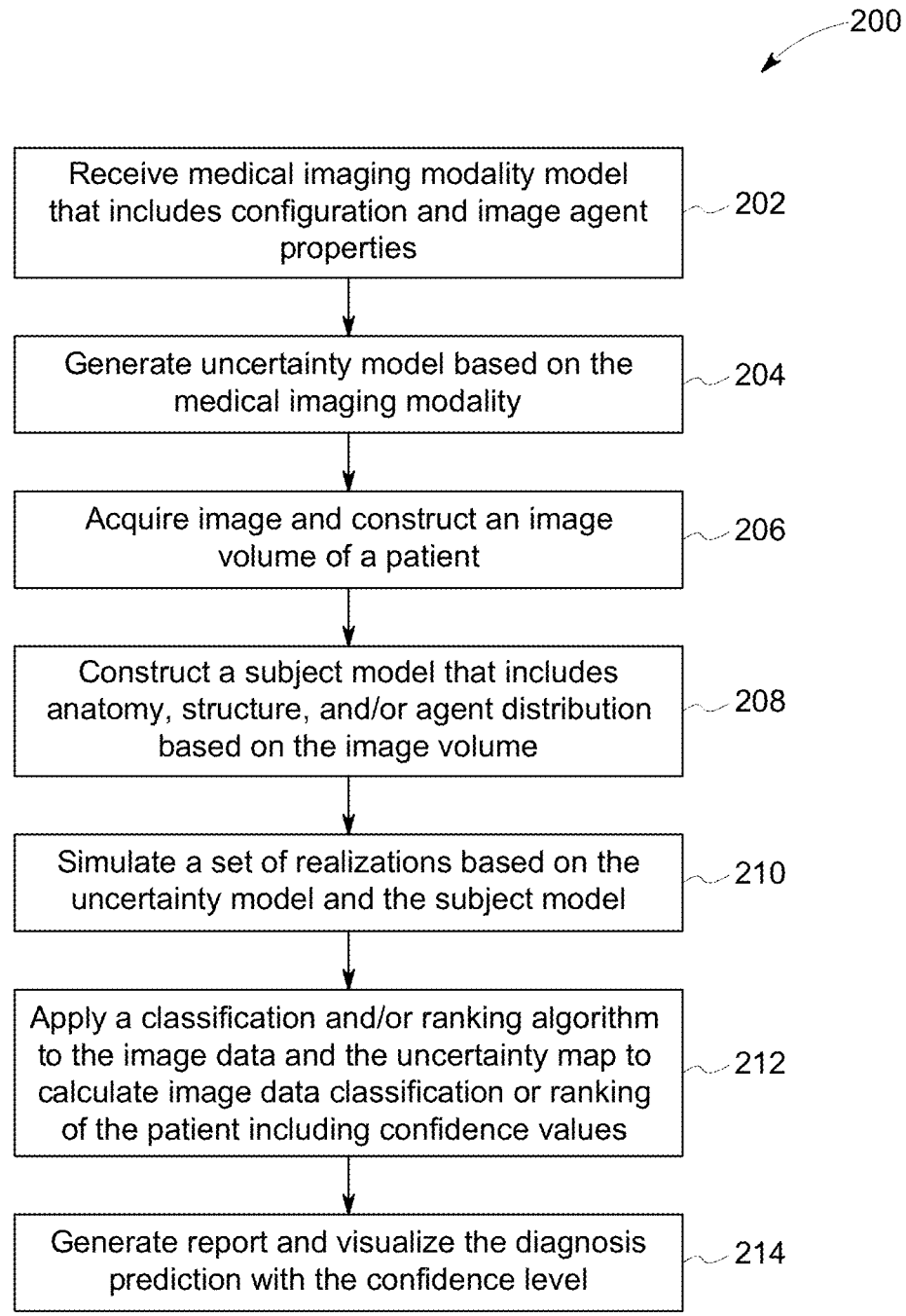
FIGS. 2A-D illustrate flow charts of embodiments of methods described herein.
Figure 2B:
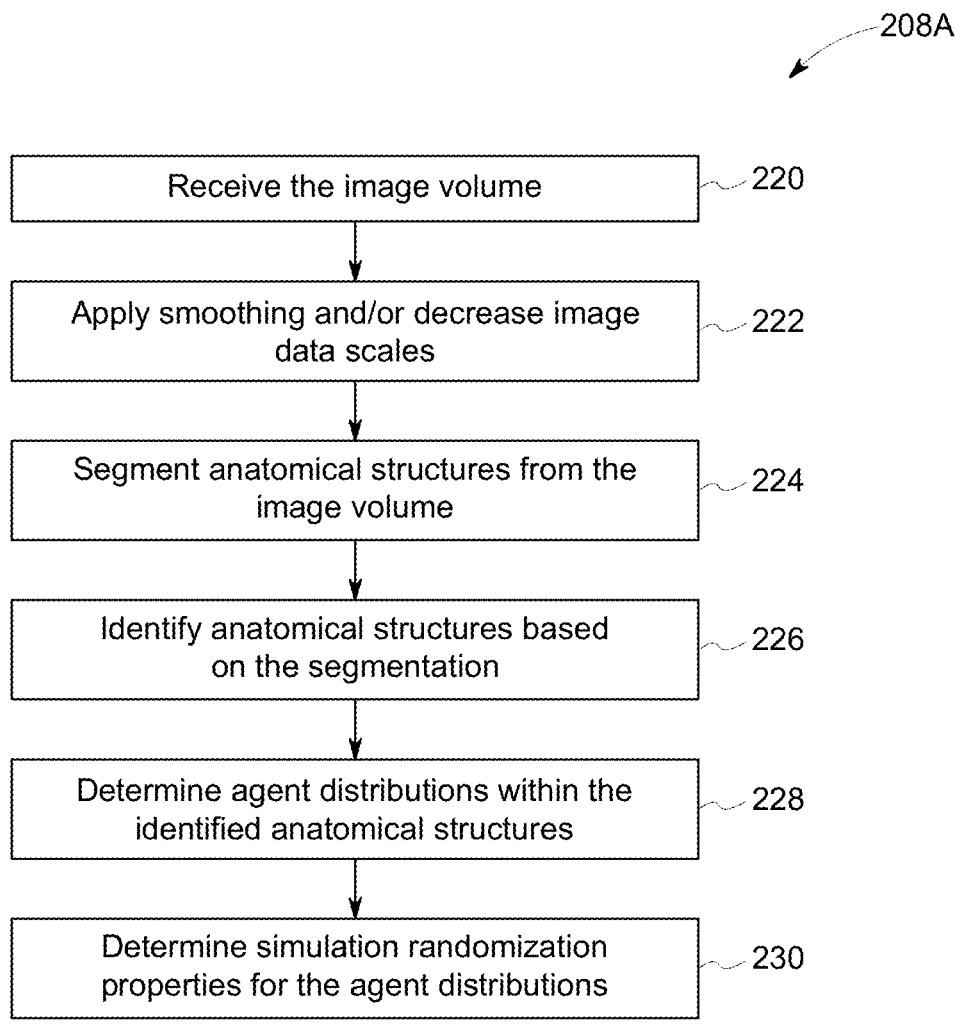

FIG. 2B provides an embodiment of the method 208a for determining the subject model. Beginning at 220, the controller circuit 105 receives the image volume formed form the operation at 206 of FIG. 2A. For example, the image volume may be stored in the memory 164.

At 222, the controller circuit 105 applies smoothing and/or decrease image data scales. The smoothing represents an image processing applied to the image volume. For example, the smoothing is configured to provide a uniform spatial resolution throughout the image volume. The decrease in the image data scales reduces a geometrical structure of the image volume in all dimensions. For example, the controller circuit 105 reduces the geometrical structure of the image volume at a set ratio stored in the memory 164.

At 224, the controller circuit 105 segments anatomical structures (e.g., bone, organs) from the image volume. For example, the controller circuit 105 segments the anatomical structures utilizing thresholds from a priori information stored in the memory 164. The thresholds may be used to distinguish between different counts representing different anatomical structures. For example, the controller circuit 105 applies a threshold for bone and/or a skeleton structure. The threshold represents an image voxel value (e.g., count value) that corresponds to bone, such as over 50 projection and/or sinogram counts. The threshold separates the bone and/or skeleton structure from background activity. Optionally, the controller circuit 105 utilizes a structural estimation subsequent to the threshold operation. For example, after the thresholding an overall shape of the anatomical structure is formed. The memory 164 includes different shapes of the anatomical structure (e.g., bond structure, organ shape). The controller circuit 105 compares the shape from the thresholded image data with the different shapes of the anatomical structures stored in the memory 164. When the outline of the shape is within a predetermined threshold (e.g., within 5%) with the shape of the anatomical structure, the controller circuit 105 identifies the anatomical structure.

At 228, the controller circuit 150 determines agent distributions within the identified anatomical structures. The agent distribution is associated with the image voxel value (e.g., the number of projection and/or sonogram counts) for a voxel region during the scan representing one of the anatomical structures. The controller circuit 105 translates the image voxel value to identify a total average number of decays (e.g., emitted photons) during the scan. For example, a first voxel region represents bone. The image voxel value of the first voxel region is 1000. The controller circuit 105 translates the image voxel value to a radioactive density in MBq/ml, which is associated as a rate of decay per second. For example, the image voxel value of 1000 is approximately 1 MBq/ml. The length of the scan time is known, such as five minutes. Based on the rate and the length of the scan, a total average number of radioactive decays (i.e. emitted gamma photons) from the first voxel region during the scan is calculated. The controller circuit 105 repeats the above process for the different anatomical structures identified at 226. Based on the different rates of the anatomical structure, the controller circuit 105 generates the subject model that corresponds as a total number of emitted gamma photons for each of the anatomical structures.

At 230, the controller circuit 105 determines simulation randomization properties for the agent distribution. The simulation randomization properties corresponds to different probabilities such as projection and/or sinogram count values based on the uncertainty model. For example, the first voxel region includes the image voxel value of 1000. The image voxel value represents a mean of the natural-statistics distribution. The controller circuit 105 randomly selects different positions along the natural-statistics distribution and/or the uncertainty model representing the different simulations. The different position along the natural-statics distribution correspond to different parameter selections of the medical imaging system 100, which adjust the inherent uncertainty of the medical imaging system 100. For example, a first simulation may represent an image voxel value of 950, a second simulation may represent an image voxel value of 1050, and/or the like. The different image voxel values correspond to the different probability values along the natural-statistics distribution and/or the uncertainty model corresponding to different projection and/or sinogram counts.

Additionally or alternatively, the times during the scan duration can be randomly selected. For example, the gamma photons may be emitted from the source not in equal time spacing (e.g., randomly varied). For the first voxel region, at a first subset of the scan length the projection and/or sinogram count is 300, and in a second subset of the scan the projection and/or sinogram count is 500. The controller circuit 105 may select the different subsets of the projection and/or sinogram counts during the scan for the simulation randomization.

Returning to FIG. 2A, at 210, the controller circuit 105 simulates a set of realizations based on the uncertainty model and the subject model. In connection with FIG. 2C, the subject model is formed based on a method 210a.

Figure 2C:
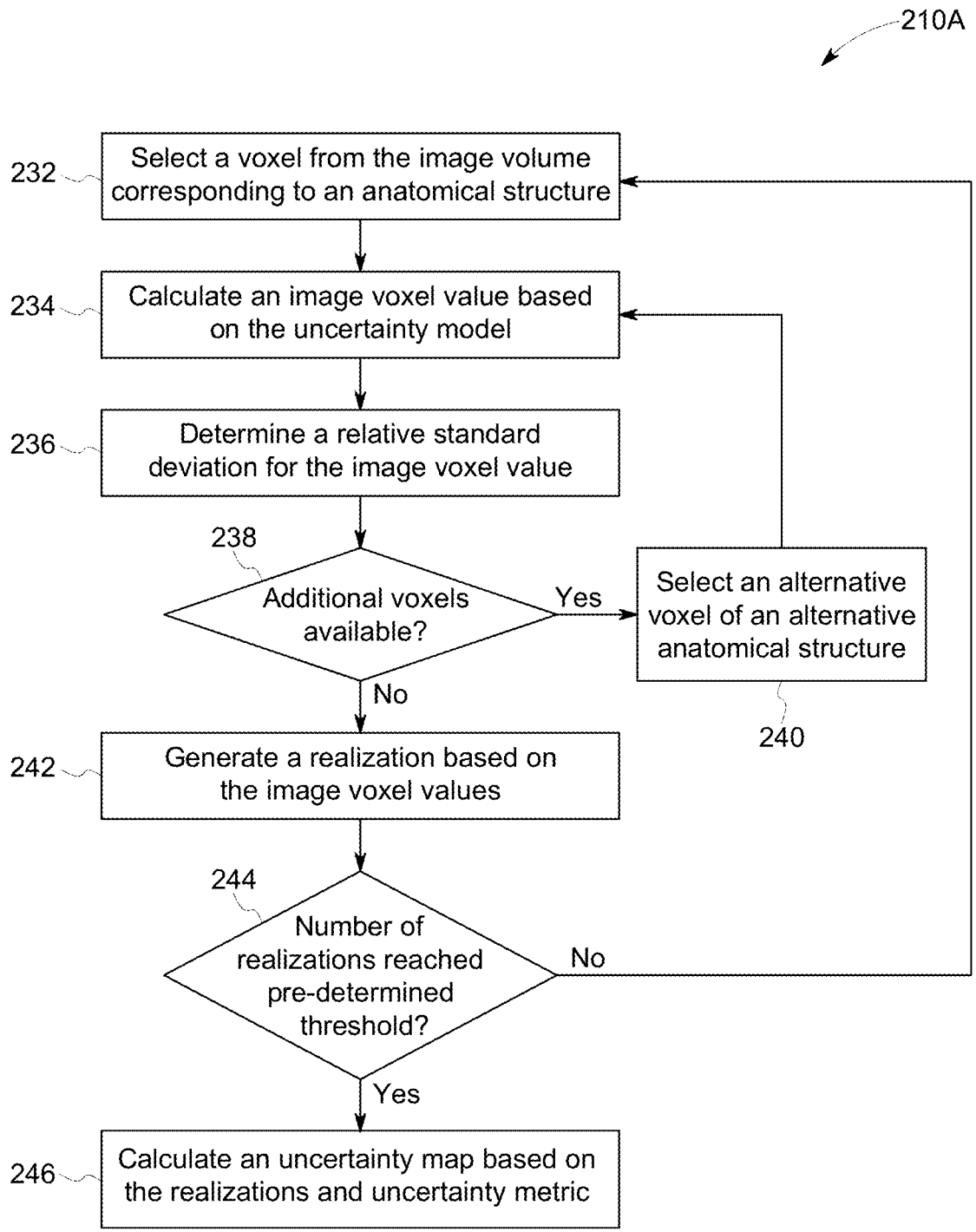

FIG. 2C provides an embodiment of the method 210a for simulating a set of realizations based on the uncertainty model and the subject model. Beginning at 232, the controller circuit 105 selects a voxel from the image volume corresponding to an anatomical structure. For example, the controller circuit 105 selects a voxel of the image volume representing a forearm 313 based on the subject model. As noted herein, the subject model includes relative positions of the anatomical structures within the image volume.

At 234, the controller circuit 105 calculates an image voxel value based on the uncertainty mode. For example, the image voxel value for the forearm 313 has a mean of 1500 (e.g., projection and/or sinogram counts). The controller circuit 105 utilizes the Poisson distribution associated with the uncertainty model to randomly select an image voxel value. For example, the controller circuit 105 randomly selects a first image voxel value of 1000 from the uncertainty model. The controller circuit 105 calculates the first image voxel value along the Poisson distribution of the uncertainty model.

At 236, the controller circuit 105 determines an uncertainty metric for the image voxel value. The uncertainty metric is indicative of the uncertainty between the realizations 302-310. Non-limiting examples of the uncertainty metric are a relative standard deviation, a variance, a $L^1$ variation function, and/or the like. For example, the uncertainty metric may represent the relative standard deviation. The relative standard deviation is based on the standard deviation of the image voxel values (e.g., forearm 313 of FIG. 3) acquired during the scan of the image volume and the image voxel value calculated at 234. For example, the standard deviation represents a variation and/or dispersion of the different projection and/or sinogram counts at the forearm 313 during the scan. The relative standard deviation is calculated based on the standard deviation divided by the image voxel value of 1000. Additionally or alternatively, the controller circuit 105 may calculate alternative statistical metrics rather than the relative standard deviation.

At 238, the controller circuit 105 determines whether additional voxels are available. For example, the controller circuit 105 identifies whether any voxels of the image map does not include the uncertainty metric and/or image voxel value based on the uncertainty model.

Figure 3:
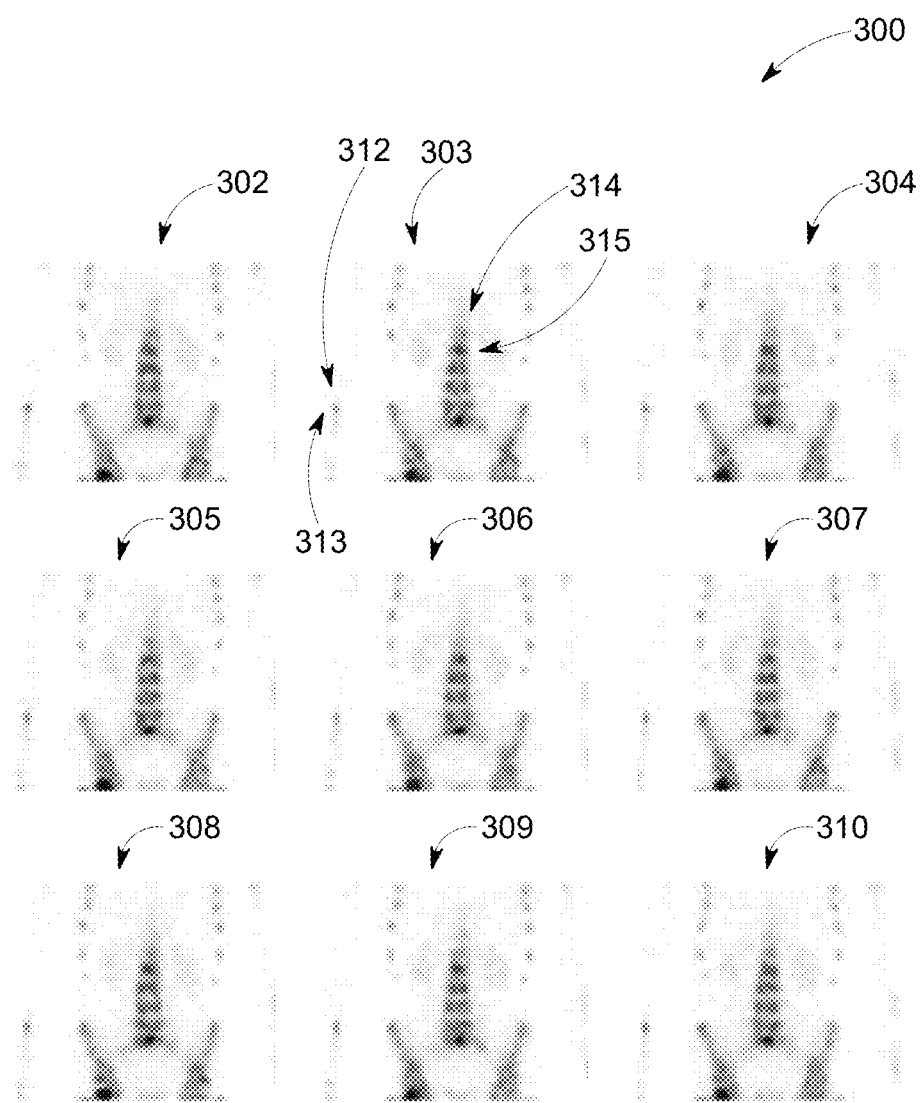
FIG. 3 illustrates an embodiment of a collection of realizations.

If additional voxels are available, then at 240, the controller circuit 105 selects an alternative voxels of an alternative anatomical structure with the image volume. Optionally, the controller circuit 105 may select an alternative voxel of the anatomical structure described at 232. For example, the controller circuit 105 utilizes the subject model to identify an alternative voxel, such as the anatomical structure representing, a spine 315 (FIG. 3). The controller circuit 105 repeats the operations at 234, 236 to identify an image voxel value based on the uncertainty model and the uncertainty metric.

If there are no additional voxels, then at 242, the controller circuit 105 generates a realization based on the image voxel values. FIG. 3 illustrates an embodiment of a collection 300 of realizations 302-310. Each of the realizations 302-310 may represent different image voxel values for the anatomical structures of the image volume. The different image voxel values represent a simulation. The realizations 302-310 represent different simulations based on selections of different image voxel values based on the uncertainty model. The controller circuit 105 generates the realizations 302-310 through various techniques (e.g., iterative reconstruction, back projection, etc.) based on the image volume.

The collection 300 includes nine realizations 302-310 for a bone scan performed by the medical imaging system 100. The realizations 302-310 include different image voxel values for the anatomical structures of the realizations 302-310. For example, the lower and upper realizations 302 and 310 may include image voxel values of the anatomical structures corresponding to lower activity and/or counts. It may be noted that the different voxels within the different spatial locations (e.g., anatomical structures) of the realizations 302-310 have a common image voxel value. For example, the realization 303 the image voxel value corresponding to the forearm 313 has a common image voxel value that is different than the image voxel value corresponding to the spine 315.

In the example of FIG. 3, the realizations 302-310 show a normal/healthy RP tracer distribution in most of the skeleton. However, the realization 303 includes localized bone lesions 312, 314 with increased tracer uptake, as compared to lower background tracer uptake in the other anatomical structures of the realizations 302, 304-310. The bone lesions 312, 314 may be related to a specific disease and/or abnormal medical condition. One or more of the realizations 302-310 (e.g., 303) may represent an accurate image projection of the image volume.

The realizations 302-310 are indicative of the estimated uncertainty level of the image volume. For example, the realizations 302-310 include different image voxel values for the anatomical structures based on the uncertainty model. Each realization 302-310 includes different image voxel values for the different anatomical structures of the image volume. For example, the forearm 313 has a different image voxel value for each of the realizations 302-310, representing the uncertainty for the forearm 313 within the image volume.

At 244, the controller circuit 105 determines whether a number of realizations 302-310 reaches a predetermined threshold. The predetermined threshold represent a number of realizations 302-310 to be generated by the controller circuit 105. The predetermined threshold is stored in the memory 164. For example, the predetermined threshold may range from 10-100 different realizations.

Figure 4:
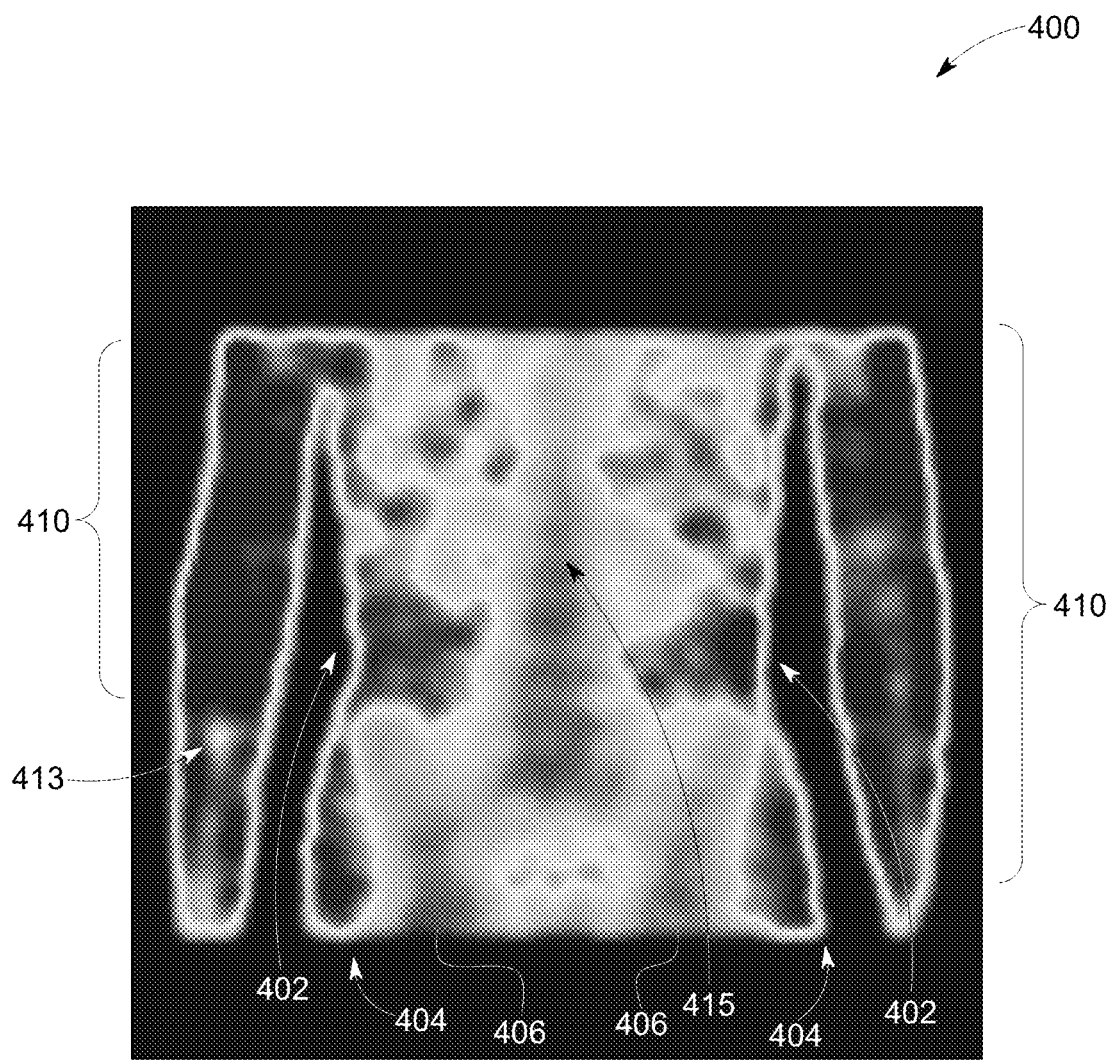
FIG. 4 illustrates an embodiment of an uncertainty map.

If the number of realizations 302-310 reaches the predetermine threshold, then at 246, the controller circuit 105 generates an uncertainty map based on the realizations 302-310 and the uncertainty metric. The uncertainty map represents a patient specific uncertainty map based on the subject model. FIG. 4 illustrates an embodiment of an uncertainty map 400. The uncertainty map 400 is a representation of the various the uncertainty metrics of the different positions of the image volume. The uncertainty metrics are calculated by the controller circuit 105, and are shown as the voxels of the uncertainty map 400 that includes the uncertainty metrics from the different realizations 302-310. For example, the uncertainty map 400 represents a combination of the realizations 302-310 formed by the controller circuit 105 with the uncertainty metrics. For example, the realizations 302-310 may be overlaid or otherwise aligned with one another such that voxels from the realizations 302-310 are aligned with one another. For example, the voxels in the realization 302 (also referred to as the first realization voxels) are aligned with voxels in the realization 303 (also referred to as the second realization voxels). The first and second realization voxels are aligned with pixels in all or at least a portion of the realizations 304-310.

Once aligned, the controller circuit 105 adjusts pixels values indicative of the uncertainty metrics of the voxels of the different spatial locations. For example, each voxel in the uncertainty map 400 includes the uncertainty metrics among the different realizations 302-310. A color of the voxel indicates a level of uncertainty of the uncertainty map 400 based on the uncertainty metrics.

For example, the uncertainty metrics represents the relative standard deviation. The color represents a range of the relative standard deviations corresponding to each voxel. For example, the controller circuit 105 identifies a range of the relative standard deviations from the realizations 302-310. The controller circuit 105 assigns a color value to the voxel that represents the range of the different relative standard deviations at the spatial position. For example, the spatial location 413 includes a yellow voxel color corresponding to the forearm 313 that represents a large range of the relative standard deviations from the realizations 302-310. In another example, the spatial locations 410 representing arms, the spatial locations 404 representing a waist, and the spatial locations 402 representing abdominal sides of the uncertainty map 400 include a red voxel color that represents a large range of the relative standard deviations from the realizations 302-310. Optionally, the spatial location 415 corresponding to the spine 315 and the spatial location 406 representing a pelvic girdle include a blue voxel color that represents a small range of the relative standard deviations from the realizations 302-310.

Optionally, the controller circuit 105 adjust parameters of the medical imaging system 100 based on the uncertainty map 400. The controller circuit 105 may adjust the selections from the uncertainty model. For example, the controller circuit 105 identifies voxels that have a high uncertainty based on the uncertainty metric. The controller circuit 105 adjusts the scan parameters defining the system matrix, which adjusts the uncertainty model. The adjustment of the scan parameters are configured to select different probabilities based on the voxels having a high uncertainty. For example, the uncertainty metric is a relative standard deviation. The forearm 313 includes a large range of relative standard deviation based on the realizations 302-310. The controller circuit 105 adjusts the probabilities based on the voxel such that the "true value" utilized for imaging is based on a mean of the voxel values. Additionally or alternatively, the controller circuit 105 is configured to re-generate the image volume based on the updated system matrix.

Returning to FIG. 2A, at 212, the controller circuit 105 applies the classification and/or ranking algorithm to the image data and the uncertainty map to calculate image data classification or ranking of the patient including confidence values. The classification and/or ranking algorithm is stored in the memory 164. The classification and/or ranking algorithm is configured to automatically calculate image data classification or ranking. The classification or ranking represents a severity ranking and/or a predicted diagnosis based on the image volume. The predicted diagnosis is indicative of a lesion, cancer, benign classes, and/or the like. Additionally, the classification and/or ranking algorithm assigns confidence values to the voxel locations based on the image volume and the uncertainty map 400. The confidence values are utilized to affirm and/or reduce a likelihood of the predicted diagnosis based on the image volume. For example, the controller circuit 105 receives the image volume and the associated uncertainty map 400 (e.g., stored in the memory 164). The controller circuit 105 may select voxels that include the predicted diagnosis (e.g., the bone lesions 312, 314). The controller circuit 105 analyzes the uncertainty map 400 corresponding to the voxel locations of the bone lesions 312, 314.

For example, the controller circuit 105 analyzes the uncertainty metric at the voxel location of the bone lesions 312, 314. The controller circuit 105 applies the classification and/or ranking algorithm to the image data and the uncertainty metric. The controller circuit 105 performs iterations on the image data in order for classification and/or ranking the image data and the confidence value. The classification and/or ranking represents a severity rank of the voxel. The severity rank is indicative of a predictive diagnosis of the voxel location. The severity rank identifies the voxel location as a lesion, cancer, benign, and/or the like. The image data and/or the uncertainty metric at the voxel location compares the range of the uncertainty metric and/or the characteristics of the voxel (e.g., intensity, brightness) to the known voxels representing unhealthy tissue. For example, the classification and/or ranking algorithm is trained utilizing known lesion, cancer, benign, and/or the like training voxels. The training voxels configure the classification and/or ranking algorithm to identify characteristics of voxels representing unhealthy tissue. For example, the controller circuit 105 identifies the bone lesions 312, 314 from the image data. The bone lesion 312, 314 have characteristics such as brightness and/or intensity that matches training voxels indicating lesion. The controller circuit 105 assigns a severity rank for the voxel locations of the bone lesions 312, 314 indicating lesions. Additionally, the classification and/or ranking is adjusted and/or based on a confidence value of the voxel location.

The controller circuit 105 calculates the confidence values based on the uncertainty metric. For example, the range of the relative standard deviation corresponding to the forearm 313 (e.g., spatial location 413) includes a large uncertainty (e.g., large range of the relative standard deviation). Based on the large uncertainty, the controller circuit 105 assigns a low confidence value to the predicted diagnosis of the bone lesion 312. The low confidence value may represent a percentage (e.g., such as below 25%), a magnitude of a scale (e.g., 25 out of 100), and/or the like. In another example, the range of the relative standard deviation corresponding to the spine 315 (e.g., spatial location 415) includes a small uncertainty (e.g., small range of the relative standard deviation). Based on the small uncertainty, the controller circuit 105 assigns a high confidence value to the predicted diagnosis of the bone lesion 314. The high confidence value may represent a percentage (e.g., such as above 85%), a magnitude of a scale (e.g., 85 out of 100), and/or the like. The controller circuit 105 can adjust the severity rank based on the confidence values. For example, the controller circuit 105 identifies the bone lesion 312 with a low confidence value. Based on the low confidence value, the controller circuit 105 adjusts the severity rank of the bone lesion 312 to indicate that the bone lesion 312 is not a lesion. In another example, the controller circuit 105 identifies the bone lesion 314 with a high confidence value. Based on the high confidence value, the controller circuit 105 affirms the severity rank of the bone lesion 314 as a lesion.

It may be noted that the confidence values are based on the training of the classification and/or ranking algorithm. For example, in an embodiment the classification and/or ranking algorithm may be configured to identify a large uncertainty at the forearm 313 includes a large confidence value.

As noted above, the uncertainty map 400 includes spatial positions of voxels that have a level of uncertainty. For example, the different uncertainty metrics for each voxel represents the level of uncertainty. Optionally, the uncertainty metric represents a relative standard deviation. A large range of the relative standard deviation corresponds to a voxel having a high level of uncertainty, such as the voxel positioned at the forearm 313 (e.g., shown as spatial location 413). Alternatively, a low range of the relative standard deviation corresponds to a voxel having a low level of uncertainty, such as the voxel positioned at the spine 315 (e.g., shown as spatial location 415).

Optionally, the controller circuit 105 identifies the high level of uncertainty as regions and/or features of interest. For example, the controller circuit 105 selects the voxel (e.g., spatial location 413) corresponding to the forearm 313 representing a high uncertainty area as a region and/or feature of interest. Additionally or alternatively, the controller circuit 105 identifies regions and/or features of interest based on the realizations 302-310. For example, the controller circuit 105 identified bone lesions 312, 314 corresponding to the forearm 313, and the spine 315, respectively. The controller circuit 105 selects the voxels corresponding to the anatomical structures based on the subject model, which includes positions of the anatomical structures relative to the image volume.

The classification and/or ranking algorithm may represent an artificial neural network that includes an input layer, a plurality of hidden layers, and an output layer. It may be noted that in other embodiments the classification and/or ranking algorithm may be a decision tree, K-means clustering, deep learning, and/or the like. Additionally or alternatively, a plurality of classification and/or ranking algorithm may be trained for specific anatomical features (e.g., arm, wrist, head, leg, stomach, lung). For example, the controller circuit 105 may segment the anatomical structures based on the subject model into corresponding classification and/or ranking algorithm that are trained for the selected anatomical structure.

Additionally or alternatively, the controller circuit 105 may adjust the confidence values 500 based on additional information of the patient, such as a pathological state and/or clinical attribute. For example, the controller circuit 105 receive a pathological state and/or clinical attributes of the patient. The pathological state is indicative of one or more previous diagnoses. For example, the pathological state may represent a fracture, metastasis, and/or the like. Based on the pathological state, the controller circuit 105 may adjust a confidence value corresponding to a severity rank representing the fracture and/or metastasis. The adjustment of the confidence value reduces a likelihood of the predicted diagnosis and/or severity rank. The clinical attributes represent historical information of the patient represented as a vector. For example, the clinical attributes can include cancer (type, grade, location), osteoporosis, age, weight, height, prior fractures (location, time of occurrence, treatment), lab tests, and/or the like. The clinical attributes are used by the controller circuit 105 for determining a negative/positive predictive value of a pathology of the patient. The negative/positive predictive value is utilized by the controller circuit 105 to adjust the confidence values. For example, a positive predictive value of a focal lesion of an anatomical feature (e.g., a rib) for the patient without prior cancer would be extremely low as compared to a 10% probability in a patient with known prior occurrences of cancer. Based on the clinical attributes, the controller circuit 105 may increase and/or decrease the confidence values for anatomical features that have a prior pathology that matches with a previously occurred diagnosis within the patient. For example, the patient has a clinical attributes of known occurrences of cancer. Based on the clinical attributes, the controller circuit 105 may increase the confidence value of the bone lesion for the forearm.

Additionally or alternatively, the controller circuit 105 may separate the image data based on the different pathologies. For example, the controller circuit 105 may separate image data based on the anatomical features that have been previously attributed to having a pathology. The separate image data can be analyzed by the controller circuit 105 separately to identify the diagnosis.

Optionally, the controller circuit 105 updates the classification and/or ranking algorithm. For example, the controller circuit 105 receives a plurality of uncertainty maps of multiple patients. The uncertainty maps may be received by the controller circuit 105 along the uni-directional and/or bi-directional communication link with the remote server, an alternative medical imaging system, and/or the like. The uncertainty maps are formed similar to and/or the same as the operation at 208 for the multiple patients. The uncertainty maps may be grouped based on different identified diagnoses for the multiple patients. The controller circuit 105 receives one of the diagnosis groups of the uncertainty maps, representing a cancerous lesion on a leg. The controller circuit 105 assumes the uncertainty map representing the cancerous lesion is truth, which is compared with an output of the classification and/or ranking algorithm stored in the memory 165. For example, the controller circuit 105 applies the uncertainty map into the classification and/or ranking algorithm. The controller circuit 105 compares the output of the classification and/or ranking algorithm with the assumed truth from the uncertainty map. For example, the controller circuit 105 calculates a loss between the output and the assumed truth. The loss is utilized to adjust the classification and/or ranking algorithm. For example only, the controller circuit 105 adjusts the weight matrixes of the hidden layers based on the loss. The controller circuit 105 may continue the process for the remaining received uncertainty maps.

Figure 5:
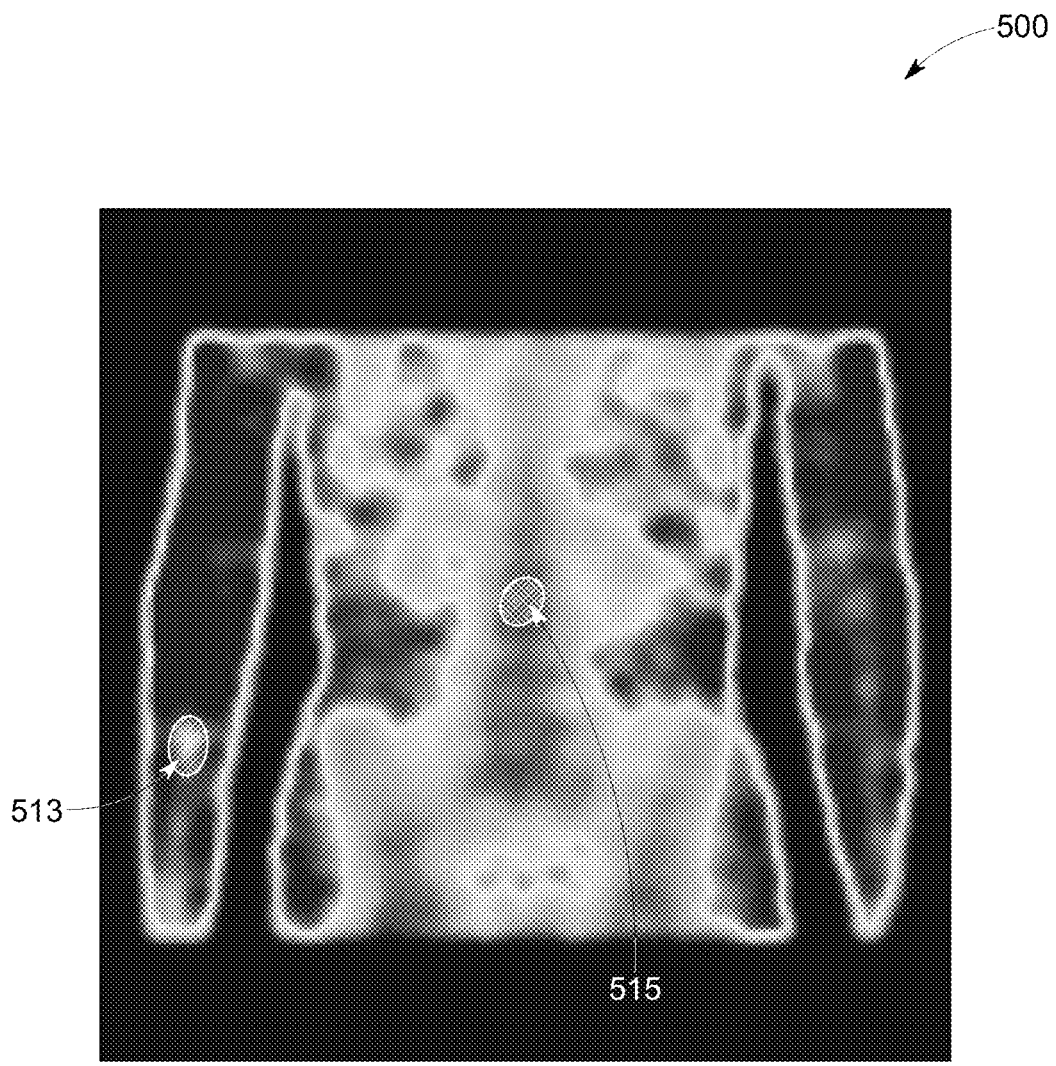
FIG. 5 illustrates an embodiment of a confidence value overlaid on an uncertainty map.

At 214, the controller circuit 105 generates a report and visualize the diagnosis prediction with the confidence level. FIG. 5 illustrates an embodiment of confidence values 500 overlaid on the image volume. The confidence values 500 may represent a percentage, magnitude, and/or the like identified by the classification or ranking algorithm. The confidence values 500 represent a likelihood that the anatomical structure is healthy and/or diseased. Optionally, the controller circuit 105 converts the confidence values that represent diseased anatomical structures as colored pixels. For example, the different colored pixels at locations 513, 515 correspond to the forearm 313 and the spine 315, respectively. For example, the forearm 313 is shown having a low confidence value for the bone lesion 312. In another example, the spine 315 is shown having a high confidence value for the bone lesion 314.

Additionally or alternatively, the controller circuit 105 may overlay confidence values 500 on an image volume based on the image data. For example, the confidence values 500 are overlaid by the controller circuit 105 as different graphical indicators (e.g., arrows, text, graphical icons) to indicate the confidence values 500 of healthy and/or diseases anatomical structures. For example, the confidence values 500 includes a pair of graphical indicators at the locations 513, 515 of the anatomical features representing diseased anatomical structures.

Additionally or alternatively, the controller circuit 105 may overlay graphical indicators representing the severity rank at one or more voxel locations. For example, the controller circuit 105 may overlay a graphical indicator at the location 515 corresponding to the spine 315. The graphical indicator is indicative of a lesion identified at the corresponding location, the spine 315.

Figure 2D:
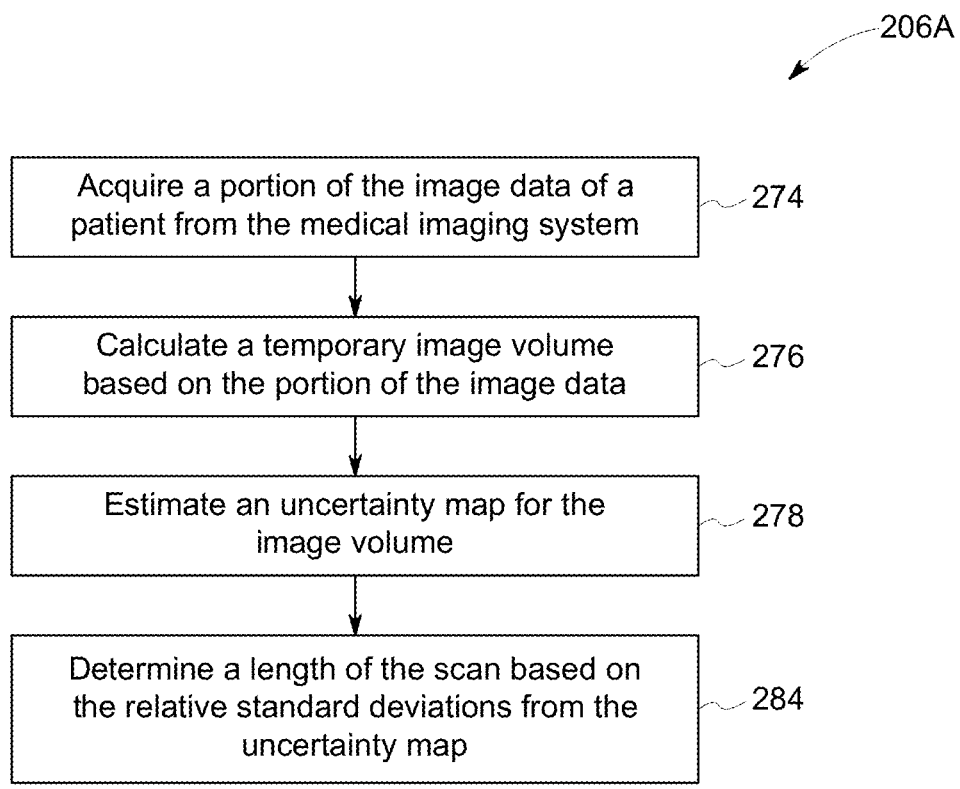

In connection with FIG. 2D, the controller circuit 105 may be configured to adjust a length of the scan to acquire the image data. For example, the controller circuit 105 may receive a user input from the user input device 166 to adjust the scan length according to the method 206A. Beginning at 274, the controller circuit 105 acquires a portion of the image data of a patient from the medical imaging system 100. The portion of the image data may correspond to a limited scan, such as a one minute scan of the patient.

At 276, the controller circuit 105 calculates a temporary image volume based on the portion of the image data. For example, the controller circuit 105 generates the temporary image volume based on the projection and/or sinogram counts acquired for the portion of the image data.

At 278, the controller circuit 105 estimates an uncertainty map for the temporary image volume. As explained herein, the controller circuit 105 utilizes the uncertainty model to generate different simulations form the portion of image data. The different simulations form realizations. The controller circuit 105 calculates relative standard deviations based on the realizations to form the uncertainty map.

At 284, the controller circuit 105 determines a length of the scan based on the relative standard deviations from the uncertainty map. The controller circuit 105 analyzes the ranges of the relative standard deviations for the voxels of the uncertainty map. For example, when the image data includes a large range of relative standard deviations, the controller circuit 105 determines that a long scan length is needed. The long scan length is utilized to assure that the additional projection and/or sinogram counts are acquired to assure an accurate subject model. In another example, when the image includes a small range of relative standard deviations, the controller circuit 105 determines that a shorter scan length can be used. Since the range of the relative standard deviations are low, the additional projection and/or sinogram counts are not needed for an accurate subject model.

Returning to FIG. 1, the table controller 134 may move the patient table 120 to position the subject 101 relative to the imaging detectors 102. The patient table 120 may be moved in up-down directions, in-out directions, and right-left directions, for example. The detector controller 136 may control movement of each of the imaging detectors 102 to move together as a group or individually. The detector controller 136 also may control movement of the imaging detectors 102 in some embodiments to move closer to and farther from a surface of the subject 101, such as by controlling translating movement of the detector carriers 116 linearly towards or away from the subject 101 (e.g., sliding or telescoping movement). Optionally, the detector controller 136 may control movement of the detector carriers 116 to allow movement of the detector array 106 or 108. For example, the detector controller 136 may control lateral movement of the detector carriers 116 illustrated by the T arrow (and shown as left and right). In various embodiments, the detector controller 136 may control the detector carriers 116 or the support members 112 to move in different lateral directions. Detector controller 136 may control the swiveling motion of detectors 102 together with their collimators 122. In some embodiments, detectors 102 and collimators 122 may swivel or rotate around an axis.

The pivot controller 138 may control pivoting or rotating movement of the detector units 114 at ends of the detector carriers 116 and/or pivoting or rotating movement of the detector carrier 116. For example, one or more of the detector units 114 or detector carriers 116 may be rotated about at least one axis to view the subject 101 from a plurality of angular orientations to acquire, for example, 3D image data in a 3D SPECT or 3D imaging mode of operation. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 101 or a portion of the subject 101, the imaging detectors 102, gantry 104, patient table 120 and/or collimators 122 may be adjusted, such as to first or initial imaging positions, as well as subsequent imaging positions. The imaging detectors 102 may each be positioned to image a portion of the subject 101. Alternatively, for example in a case of a small size subject 101, one or more of the imaging detectors 102 may not be used to acquire data, such as the imaging detectors 102 at ends of the detector arrays 106 and 108, which as illustrated in FIG. 1 are in a retracted position away from the subject 101. Positioning may be accomplished manually by the operator and/or automatically, which may include using, for example, image information such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector units 114 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 102, gantry 104, patient table 120, and/or collimators 122 are positioned, one or more images, such as three-dimensional (3D) SPECT images are acquired using one or more of the imaging detectors 102, which may include using a combined motion that reduces or minimizes spacing between detector units 114. The image data acquired by each imaging detector 102 may be combined and reconstructed into a composite image or 3D images in various embodiments.

In one embodiment, at least one of detector arrays 106 and/or 108, gantry 104, patient table 120, and/or collimators 122 are moved after being initially positioned, which includes individual movement of one or more of the detector units 114 (e.g., combined lateral and pivoting movement) together with the swiveling motion of detectors 102. For example, at least one of detector arrays 106 and/or 108 may be moved laterally while pivoted. Thus, in various embodiments, a plurality of small sized detectors, such as the detector units 114 may be used for 3D imaging, such as when moving or sweeping the detector units 114 in combination with other movements.

In various embodiments, a data acquisition system (DAS) 160 receives electrical signal data produced by the imaging detectors 102 and converts this data into digital signals for subsequent processing. However, in various embodiments, digital signals are generated by the imaging detectors 102. An image reconstruction device 162 (which may be a processing device or computer) and the memory 164 may be provided in addition to the controller circuit 105. It should be noted that one or more functions related to one or more of data acquisition, motion control, data processing and image reconstruction may be accomplished through hardware, software and/or by shared processing resources, which may be located within or near the medical imaging system 100, or may be located remotely. DAS 160 receives the acquired images from detectors 102 together with the corresponding lateral, vertical, rotational and swiveling coordinates of gantry 104, support members 112, detector units 114, detector carriers 116, and detectors 102 for accurate reconstruction of an image including 3D images and their slices.

In an embodiment a method is provided. The method includes defining an uncertainty model of a medical imaging system. The uncertainty model is based on natural-statistics distribution of the medical imaging system response. The method includes acquiring image data of a patient from the medical imaging system, and calculating an uncertainty map of the patient based on the uncertainty model and the image data. The uncertainty map represents a collection of realizations that are generated based on the image data and the uncertainty model. The method includes applying a classification or ranking algorithm to the image data and the uncertainty map to calculate image data classification or ranking of the patient including confidence values.

Optionally, the different realizations are based on simulations of selections from the uncertainty model. The simulations automatically randomize parameters of the medical imaging system response to select different image voxel values. Additionally or alternatively, the method includes calculating an uncertainty metric based on the different realizations. A range of the uncertainty metric is used in the calculating operation of the confidence values. Additionally or alternatively, the classification or ranking represents a severity ranking of the image data. Optionally, the method includes overlaying confidence values on an image volume based on the image data. The confidence values are based on at least one of the realizations. Optionally, the method includes determining a length of a scan of the patient based on a temporary image volume. Optionally, the method includes adjusting parameters of the medical imaging system based on the uncertainty map. The parameters adjust the inherent uncertainty of the medical imaging system. Optionally, the method includes receiving a pathological state of the patient, and adjusting at least one confidence value. The confidence value is based on the pathological state. Additionally or alternatively, the method includes receiving a plurality of uncertainty maps for multiple patients, and adjusting the classification or ranking algorithm based on the plurality of uncertainty maps. The classification or ranking algorithm is adjusted to identify features of the plurality of uncertainty maps representing medical condition relating to one or more diagnoses.

In an embodiment a medical imaging system is provided. The system includes plurality of detector units disposed about a gantry configured to acquire image data of a patient, and a memory that includes a classification or ranking algorithm. The system includes at least one processor operably coupled to the detector units. The at least one processor is configured to define an uncertainty model of a medical imaging system. The uncertainty model is based on natural-statistics distribution of the medical imaging system response. The at least one processors is configured to acquire image data of a patient from the medical imaging system, and calculate an uncertainty map of the patient based on the uncertainty model and the image data. The uncertainty map represents a collection of realizations that are generated based on the image data and the uncertainty model. The at least one processor is configured to apply a classification or ranking algorithm to the image data and the uncertainty map to calculate image data classification or ranking of the patient including confidence values.

Optionally, the different realizations are based on simulations of selections from the uncertainty model. The simulations automatically randomize parameters of the medical imaging system to select different image voxel values. Optionally, the at least one processor is configured to calculate an uncertainty metric based on the different realizations. A range of the uncertainty metric is used to calculate the confidence values. Additionally or alternatively, the classification or ranking represents a severity ranking of the image data. Optionally, the at least one processor is configured to overlay confidence values on an image volume based on the image data. The confidence values are based on at least one of the realizations. Additionally or alternatively, the at least one processor is configured to determine a length of a scan of the patient based on a temporary image volume. Optionally, the at least one processor is configured to adjust parameters of the medical imaging system based on the uncertainty map. The parameters adjust the inherent uncertainty of the medical imaging system. Additionally or alternatively, the at least one processor is configured to receive a non-pathological states of the patient, and adjusting at least one confidence value on the uncertainty map, wherein the confidence value is based on the non-pathological states. Optionally, the at least one processor is configured to receive a plurality of uncertainty maps for multiple patients, and adjust the classification or ranking algorithm based on the plurality of uncertainty maps. The classification or ranking algorithm is adjusted to identify features of the plurality of uncertainty maps representing medical condition relating to one or more diagnoses.

In an embodiment a tangible and non-transitory computer readable medium is provided. The tangible and non-transitory computer readable medium includes one or more programmed instructions configured to direct one or more processors. The one or more processors are directed to define an uncertainty model of a medical imaging system. The uncertainty model is based on natural-statistics distribution of the medical imaging system response. The one or more processors are directed to acquire image data of a patient from the medical imaging system, and calculate an uncertainty map of the patient based on the uncertainty model and the image data. The uncertainty map represents a collection of realizations that are generated based on the image data and the uncertainty model. The one or more processors are directed to applying a classification or ranking algorithm to the image data and the uncertainty map to calculate image data classification or ranking of the patient including confidence values.

Optionally, the different realizations are based on simulations from the uncertainty model. The simulations automatically randomize parameters of the medical imaging system to select different image voxel values.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
   defining an uncertainty model of a medical imaging system, wherein the uncertainty model is based on a natural-statistics distribution of the medical imaging system;
   acquiring image data of a patient from the medical imaging system;
   calculating an uncertainty map of the patient based on the uncertainty model and the image data, wherein the uncertainty map represents a collection of realizations that are generated based on the image data and the uncertainty model; and
   applying a classification or ranking algorithm to the image data and the uncertainty map to calculate image data classification or ranking of the patient including confidence values,
   wherein the realizations are based on simulations of selections from the uncertainty model, the simulations automatically randomize parameters of the medical imaging system to select different image voxel values.

2. The method of claim 1, wherein the classification or ranking represents a severity ranking of the image data.

3. The method of claim 1, further comprising determining a length of a scan of the patient based on a temporary image volume.

4. The method of claim 1, further comprising adjusting parameters of the medical imaging system based on the uncertainty map, wherein the parameters adjust the uncertainty model of the medical imaging system.

5. The method of claim 1, further comprising receiving a pathological state of the patient, and adjusting at least one of the confidence values based on the pathological state.

6. The method of claim 1, further comprising receiving a plurality of uncertainty maps for multiple patients, and adjusting the classification or ranking algorithm based on the plurality of uncertainty maps, wherein the classification or ranking algorithm is adjusted to identify features of the plurality of uncertainty maps representing a medical condition relating to one or more diagnoses.

7. A method comprising:
   defining an uncertainty model of a medical imaging system, wherein the uncertainty model is based on a natural-statistics distribution of the medical imaging system;
   acquiring image data of a patient from the medical imaging system;
   calculating an uncertainty map of the patient based on the uncertainty model and the image data, wherein the uncertainty map represents a collection of realizations that are generated based on the image data and the uncertainty model;
   applying a classification or ranking algorithm to the image data and the uncertainty map to calculate image data classification or ranking of the patient including confidence values; and
   calculating an uncertainty metric based on the realizations, wherein a range of the uncertainty metric is used in the calculating operation of the confidence values.

8. A method comprising:
   defining an uncertainty model of a medical imaging system, wherein the uncertainty model is based on a natural-statistics distribution of the medical imaging system;
   acquiring image data of a patient from the medical imaging system;
   calculating an uncertainty map of the patient based on the uncertainty model and the image data, wherein the uncertainty map represents a collection of realizations that are generated based on the image data and the uncertainty model;
   applying a classification or ranking algorithm to the image data and the uncertainty map to calculate image data classification or ranking of the patient including confidence values; and
   overlaying the confidence values on an image volume based on the image data, wherein the confidence values are based on at least one of the realizations.

9. A medical imaging system, comprising:
   a plurality of detector units disposed about a gantry configured to acquire image data of a patient;
   a memory that includes a classification or ranking algorithm; and
   at least one processor operably coupled to the detector units, the at least one processor configured to:
     define an uncertainty model of a medical imaging system, wherein the uncertainty model is based on a natural-statistics distribution of the medical imaging system;

acquire image data of a patient from the medical imaging system;

calculate an uncertainty map of the patient based on the uncertainty model and the image data, wherein the uncertainty map represents a collection of realizations that are generated based on the image data and the uncertainty model; and apply the classification or ranking algorithm to the image data and the uncertainty map to calculate image data classification or ranking of the patient including confidence values, wherein the realizations are based on simulations of selections from the uncertainty model, the simulations automatically randomize parameters of the medical imaging system to select different image voxel values.

10. The medical imaging system of claim 9, wherein the classification or ranking represents a severity ranking of the image data.

11. The medical imaging system of claim 9, wherein the at least one processor is configured to determine a length of a scan of the patient based on a temporary image volume.

12. The medical imaging system of claim 9, wherein the at least one processor is configured to adjust parameters of the medical imaging system based on the uncertainty map, wherein the parameters adjust the uncertainty model of the medical imaging system.

13. The medical imaging system of claim 9, wherein the at least one processor is configured to receive a pathological state of the patient and adjust at least one of the confidence values based on the pathological state.

14. The medical imaging system of claim 9, wherein the at least one processor is configured to receive a plurality of uncertainty maps for multiple patients and adjust the classification or ranking algorithm based on the plurality of uncertainty maps, wherein the classification or ranking algorithm is adjusted to identify features of the plurality of uncertainty maps representing a medical condition relating to one or more diagnoses.

15. A medical imaging system, comprising:
a plurality of detector units disposed about a gantry configured to acquire image data of a patient;
a memory that includes a classification or ranking algorithm; and
at least one processor operably coupled to the detector units, the at least one processor configured to:
define an uncertainty model of a medical imaging system, wherein the uncertainty model is based on a natural-statistics distribution of the medical imaging system;
acquire image data of a patient from the medical imaging system;
calculate an uncertainty map of the patient based on the uncertainty model and the image data, wherein the uncertainty map represents a collection of realizations that are generated based on the image data and the uncertainty model;
calculate an uncertainty metric based on the realizations; and
and
apply the classification or ranking algorithm to the image data and the uncertainty map to calculate image data classification or ranking of the patient including confidence values, wherein a range of the uncertainty metric is used to calculate the confidence values.

16. A medical imaging system, comprising:
a plurality of detector units disposed about a gantry configured to acquire image data of a patient;
a memory that includes a classification or ranking algorithm; and
at least one processor operably coupled to the detector units, the at least one processor configured to:
define an uncertainty model of a medical imaging system, wherein the uncertainty model is based on a natural-statistics distribution of the medical imaging system;
acquire image data of a patient from the medical imaging system;
calculate an uncertainty map of the patient based on the uncertainty model and the image data, wherein the uncertainty map represents a collection of realizations that are generated based on the image data and the uncertainty model;
apply the classification or ranking algorithm to the image data and the uncertainty map to calculate image data classification or ranking of the patient including confidence values; and
overlay the confidence values on an image volume based on the image data, wherein the confidence values are based on at least one of the realizations.

17. A tangible and non-transitory computer readable medium comprising one or more programmed instructions configured to direct one or more processors to:
define an uncertainty model of a medical imaging system, wherein the uncertainty model is based on a natural-statistics distribution of the medical imaging system;
acquire image data of a patient from the medical imaging system;
calculate an uncertainty map of the patient based on the uncertainty model and the image data, wherein the uncertainty map represents a collection of realizations that are generated based on the image data and the uncertainty model; and
applying a classification or ranking algorithm to the image data and the uncertainty map to calculate image data classification or ranking of the patient including confidence values,
wherein the realizations are based on simulations from the uncertainty model, the simulations automatically randomize parameters of the medical imaging system to select different image voxel values.

* * * * *